United States Patent
Cui et al.

(10) Patent No.: US 10,465,042 B2
(45) Date of Patent: *Nov. 5, 2019

(54) POLY(AMINE-CO-ESTER) NANOPARTICLES AND METHODS OF USE THEREOF

(71) Applicant: Yale University, New Haven, CT (US)

(72) Inventors: Jiajia Cui, New Haven, CT (US); Junwei Zhang, New Haven, CT (US); W. Mark Saltzman, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/152,228

(22) Filed: May 11, 2016

(65) Prior Publication Data
US 2016/0251477 A1 Sep. 1, 2016

Related U.S. Application Data

(63) Continuation-in-part of application No. 14/988,538, filed on Jan. 5, 2016, now Pat. No. 9,567,430, which is a continuation of application No. 14/293,733, filed on Jun. 2, 2014, now Pat. No. 9,272,043, which is a continuation-in-part of application No. PCT/US2012/067447, filed on Nov. 30, 2012.

(60) Provisional application No. 61/566,412, filed on Dec. 2, 2011, provisional application No. 61/870,497, filed on Aug. 27, 2013.

(51) Int. Cl.
A61K 31/7088 (2006.01)
A61K 9/51 (2006.01)
C12N 15/113 (2010.01)
C08G 63/685 (2006.01)
C12N 15/11 (2006.01)

(52) U.S. Cl.
CPC .......... *C08G 63/685* (2013.01); *C12N 15/111* (2013.01); *A61K 9/5153* (2013.01); *C12N 2310/14* (2013.01); *C12N 2320/32* (2013.01)

(58) Field of Classification Search
CPC .. C07K 1/145; C07K 1/30; G01N 2021/6417; G01N 33/6803; A61K 9/5153; C08G 63/685; C12N 15/111; C12N 2310/14; C12N 2320/32
USPC ....................................................... 424/490
See application file for complete search history.

(56) References Cited

U.S. PATENT DOCUMENTS

| | | |
|---|---|---|
| 5,034,506 A | 7/1991 | Summerton |
| 5,118,528 A | 6/1992 | Fessi |
| 5,142,047 A | 8/1992 | Summerton |
| 5,166,315 A | 11/1992 | Summerton |
| 5,217,866 A | 6/1993 | Summerton |
| 5,506,337 A | 4/1996 | Summerton |
| 5,521,063 A | 5/1996 | Summerton |
| 5,527,675 A | 6/1996 | Coull |
| 5,539,082 A | 7/1996 | Nielsen |
| 5,623,049 A | 4/1997 | Lobberding |
| 5,698,546 A | 12/1997 | Bridger |
| 5,698,685 A | 12/1997 | Summerton |
| 5,714,331 A | 2/1998 | Buchardt |
| 5,736,336 A | 4/1998 | Buchardt |
| 5,773,571 A | 6/1998 | Nielsen |
| 5,786,571 A | 7/1998 | Bethel |
| 6,849,272 B1 | 2/2005 | Langer |
| 9,272,043 B2 * | 3/2016 | Saltzman ............... A61K 47/34 |
| 2004/0242831 A1 | 12/2004 | Tian |
| 2007/0219122 A1 | 9/2007 | Glazer |
| 2008/0050920 A1 | 2/2008 | Kawahara |
| 2008/0166382 A1 | 7/2008 | Hsieh |
| 2011/0008451 A1 | 1/2011 | Saltzman |
| 2011/0262406 A1 | 10/2011 | Campo |
| 2011/0268810 A1 | 11/2011 | Saltzman |

FOREIGN PATENT DOCUMENTS

| | | |
|---|---|---|
| FR | 2873570 | 2/2006 |
| WO | 1993012096 | 6/1993 |
| WO | 2002010142 | 2/2002 |
| WO | 2004073617 | 9/2004 |
| WO | 2013176772 | 11/2013 |
| WO | 2014018423 | 6/2014 |

OTHER PUBLICATIONS

Zhou et al. Nat. Mater., 11 (1): 82-90, (2012).*
Wei et al. International Journal of Pharmaceutics 381 (2009) 1-18. (Year: 2009).*
Al-Dosari, et al., "Nonviral gene delivery: principle, limitations, and recent progress" , AAPS J.,11:671-81 (2009).
Bagha, et al., "Cleavable surfactants" , Curr Opt Colliod, 12:81-91 (2007).
Biomedical Engineering Society , Excerpts from the program book, 3 pages, 2015 Annual Meeting Oct. 7-10 , Tampa Florida (2015).
Braasch, et al., "Locked nucleic acid (LNA): fine-tuning the recognition of DNA and RNA" , Chem. Biol., 8(1):1-7 (2001).

(Continued)

Primary Examiner — Janet L Epps-Smith
(74) Attorney, Agent, or Firm — Pabst Patent Group LLP

(57) ABSTRACT

Polymers including poly(amine-co-ester), poly(amine-co-amide), or a combination thereof, and nanoparticles, particularly solid core nanoparticles, formed therefrom are provided. Solid core nanoparticles fabricated from hydrophobic polymers often require the presence of cationic complexing agents to stabilize negatively charged active agents such as siRNA. However, complexing agents are optional in the disclosed formulations because the nanoparticles contain cationic amines to stabilize negatively charged nucleic acids and hydrophobic domains to condense the nucleic acid into the core of the formed nanoparticles, thus improving encapsulation efficiency. This increase in nucleic acid loading allows the disclosed solid core nanoparticles to deliver more nucleic acid per cell without increasing total polymer delivered, further reducing cytotoxicity. Pharmaceutical compositions including an effective amount of the nanoparticles are also provided, and be used, for example, for in vitro and in vivo delivery of nucleic acids.

16 Claims, 3 Drawing Sheets

(56) References Cited

OTHER PUBLICATIONS

Chen, et al., "Novel pH-sensitive cationic lipids with linear ortho ester linkers for gene delivery", Eu J Med Chem., 52:159-72 (2012).
Chen, et al., "Targeted nanoparticles deliver siRNA to melanoma", J. Invest. Dermatol., 130: 2790-8 (2010).
Cui, et al., "Design of polymeric nanoparticles for the delivery of SiRMA to vascular endothellum", Poster presented Oct. 9 at the BMES 2015 annual meeting Oct. 7-10, Tampa Florida (2015).
Davanloo, et al., "Cloning and expression of the gene for bacteriophage T7 RNA polymerase", PNAS, 81:2035-39 (1984).
Fahmy, et al., "Surface modification of biodegradable polyesters with fatty acid conjugates for improved drug targeting", Biomaterials, 26:5727-36, (2005).
Felgner, et al., "Enhanced gene delivery and mechanism studies with a novel series of cationic lipid formulations", J. Biol. Chem., 269:2550-61 (1994).
Felgner, et al., "Lipofection: a highly efficient, lipid-mediated DNA-transfection procedure", PNAS, 84:7413-7 (1987).
Gao, et al., Nonviral gene delivery: what we know and what is next AAPS J., 9:E92-E104 (2007).
Gao, et al., "The association of autophagy with polyethylenimine-induced cytotoxicity in nephritic and hepatic cell lines", Biomaterials, 32:8613-25 (2011).
Harris, et al., "Tissue-specific gene delivery via nanoparticle coating", Biomaterials, 31:998-1006 (2010).
Hu, et al., "Reaction parameters of targeted gene repair in mammalian cells", Mol. Biotech., 29:197-210 (2005).
International Search Report for PCT application PCT/US2015/061375 dated Feb. 12, 2016.
Jiang, "Lipase-catalyzed synthesis of poly(amine-co-esters) via copolymerization of diester with amino-substituted diol", Biomacromolecules,11:1089-93 (2010).
Jin, et al., "Current progress im gene delivery technology based om chemical methods and nano-carriers", Theranostics, 4(3):24055 (2014).
Kafil, et al., "Cytotoxic impacts of linear and branched polyethylenimine nanostructures in a431 cells", BioImpacts, 1:23-30 (2011).
Liu, et al., "Enzyme-synthesized poly(amine-co-esters) as nonviral vectors for gene delivery", J Biomedmater Res A, 96A(2):456-65 (2011).
Liu, et al., "Hydrodynamics-based transfection in animals by systemic administration of plasmid DNA", Gene Ther., 6:1258-66 (1999).
Liu, et al., "Poly(omega-pentadecalactone-co-butylene-co-succinate) nanoparticles as biodegradable carriers for camptothecin delivery", Biomaterials, 30:5707-19 (2009).
Luten, et al., "Biodegradable polymers as non-viral carriers for plasmid DNA delivery", J Cont. Rel., 126:97-100 (2008).
Lv, et al., "Toxicity of cationic lipids and cationic polymers in gene delivery", J Contr. Rel., 114:100-9 (2006).
Martinez, et al., "Single-stranded antisense siRNAs guide target RNA cleavage in RNAi", Cell, 110:563-74 (2002).
McNeer, et al., "Nanopartictes deliver triplex-forming PNAs for site-specific genomic recombination in CD34+ human hematopoietic progenitors", Mol. Ther. 19:172-80 (2011).
Nagayama, et al., "Time-dependent changes in opsonin amount associated on nanoparticles alter their hepatic uptake characteristics", Int. J. Pharm., 342:215-21 (2007).
Nicol, et al., "Poly-L-glutamate, an anionic polymer, enhances transgene expression for plasmids delivered by intramuscular injection with in vivo electroporation", Gene. Ther., 9:1351-8 (2002).
Nykanen, et al., "ATP requirements and small interfering RNA structure in the RNA interference pathway", Cell, 107:309-21 (2001).
Olsen, et al., "Genomic sequence correction by single-stranded DNA oligonucleotides: role of DNA synthesis and chemical modifications of the oligonucleotide ends", J. Gene Med., 7:1534-44 (2005).
Schlegel, et al., "Anionic polymers for decreased toxicity and enhanced in vivo delivery of siRNA complexed with cationic liposomes", J. Contr. Rel., 152:393-401 (2011).
Sterchak, et al., "Uncharged stereoregular nucleic acid analogs. 1. Synthesis of a cytosine-containing oligomer with carbamate internucleoside linkages", Organic Chem., 52:4202, (1987).
Templeton, et al, "Improved DNA: liposome complexes for increased systemic delivery and gene expression", Nat. Biotechnol., 15:647-52 (1997).
Tros De Ilarduya, et al., "Gene delivery by lipoplexes and polyplexes", Eur. J. Pharm. Sci., 40:159-70 (2010).
Voevodina, Rt Al., "Exploring the solid state properties of enzymatic Poly(amine-co-ester) terpolymers to expand their applications in gene transfertion", RSC Adv., 4 (18):8953-61 (2014).
Wang, et al., "Synthesis and characterization of cationic micelles self-assembled from a biodegradable copolymer for gene delivery", Biomacromolecules, 8:1028-37 (2008).
Wang, et al., "The self-assembly of biodegradable cationic polymer micelles as vectors for gene transfection", Biomaterials, 28:5358-68 (2007).
Weising, et al.,"Foreign genes in plants: transfer, structure, expression, and applications", Ann. Rev. Genetics, 22:421 (1988).
Woodrow, et al., "Intravaginal gene silencing using biodegradable polymer nanoparticles densely loaded with small-interfering RNA", Nat Mater, 8:526-33 (2009).
Zhang, et al., "(491a) Biodegradable, multifunctional Poly(amine-co-ester) with ortho ester in the main chain for the delivery of plasmid DNA and siRNA", AICHE comference proceedings 2014 annual meeting.
Zhang, et al., "Galactosylated ternary DNA/polyphosphoramidate nanoparticles mediate high gene transfection efficiency in hepatocytes", J. Controlled Release, 102:749-63 (2005).
Zhou, et al., "Biodegradable poly(amine-co-ester) terpolymers for targeted gene deliver", Nat Mater., 11(1):82-90 (2012).
Zhong et al., Journal of Controlled Release, 2005, 109, 317-329.

* cited by examiner

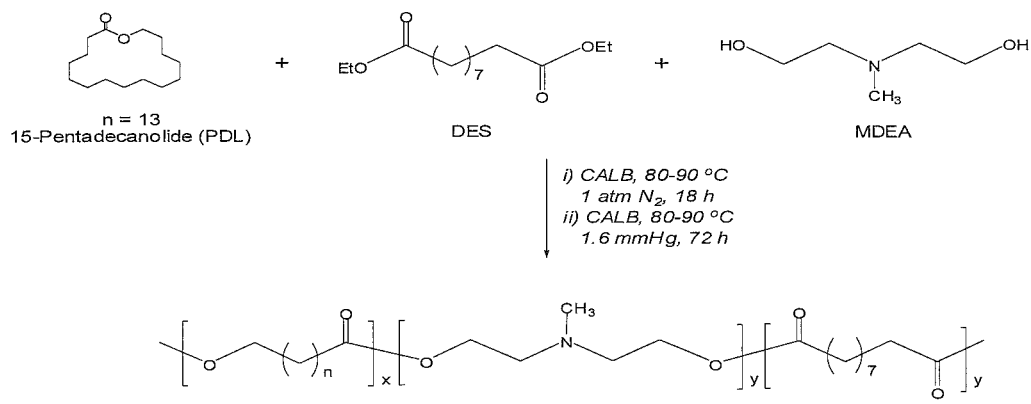
FIG. 1A
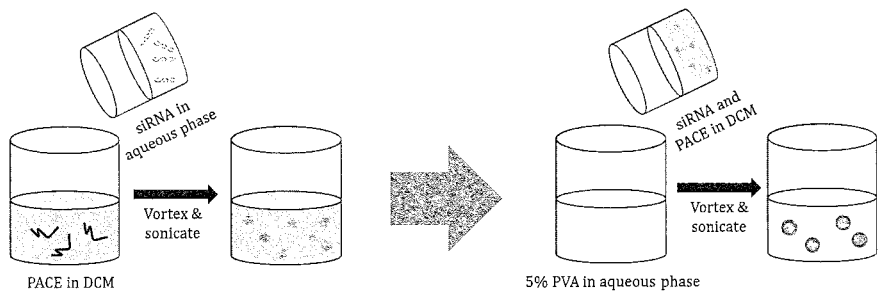
FIG. 1B
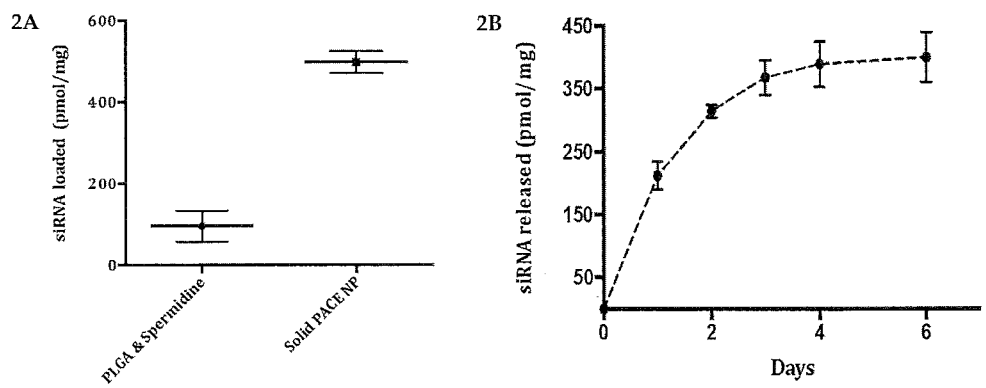
FIG. 2A
FIG. 2B

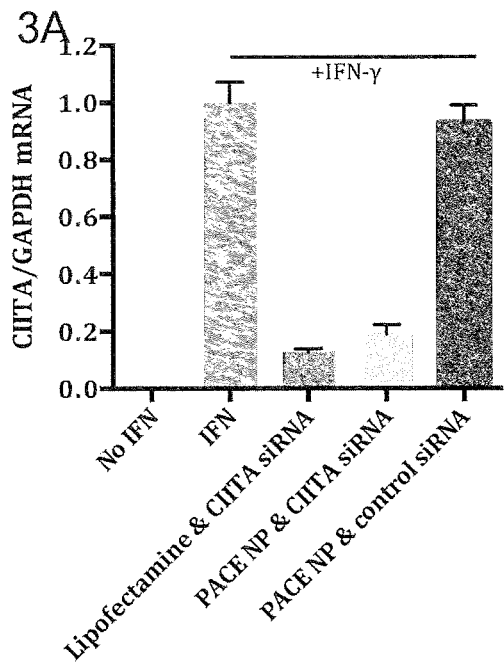
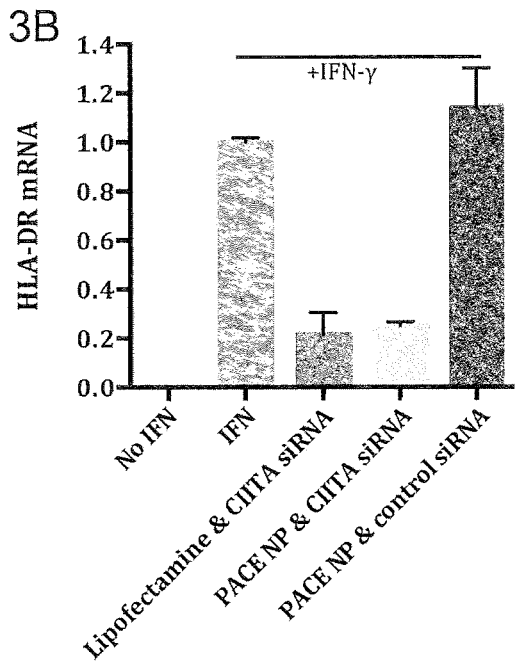
FIG. 3A	FIG. 3B
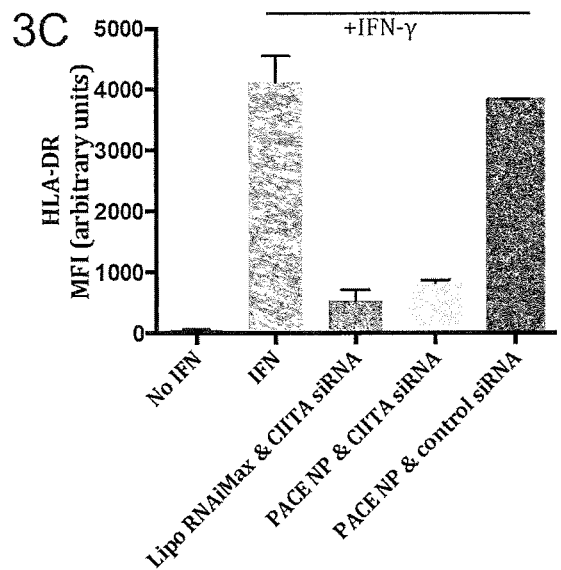
FIG. 3C

POLY(AMINE-CO-ESTER) NANOPARTICLES AND METHODS OF USE THEREOF

CROSS-REFERENCE TO RELATED APPLICATIONS

This application is a continuation-in-part of U.S. Ser. No. 14/988,538 filed Jan. 5, 2016, which is a continuation of U.S. Ser. No. 14/293,733, filed Jun. 2, 2014, now U.S. Pat. No. 9,272,043, which claims the benefit of provisional application U.S. Ser. No. 61/870,497, filed Aug. 27, 2013 and which is a continuation-in-part of PCT/US12/67447 filed Nov. 30, 2012, which claims the benefit of provisional application U.S. Ser. No. 61/566,412, filed Dec. 2, 2011, each of which is specifically incorporated by reference herein in its entirety.

STATEMENT REGARDING FEDERALLY SPONSORED RESEARCH

This invention was made with government support under AI106992 and HL085416 awarded by National Institutes of Health. The government has certain rights in the invention.

FIELD OF THE INVENTION

The field of the invention is generally related to poly(amine-co-ester) polymeric nanoparticles, methods of making nanoparticles, and methods of use thereof for improved delivery of diagnostic, prophylactic and/or therapeutic agents, particularly nucleic acid-based agents, in vitro and in vivo.

BACKGROUND OF THE INVENTION

With the discovery of RNA interference in 1998, small interfering RNAs (siRNAs) have been used to silence many genes in vivo and hold tremendous therapeutic potential in numerous clinical applications (Gavrilov, *Yale Journal of Biology and Medicine*, 85(2):187 (2012)). However, siRNAs are unstable and are degraded by serum enzymes and intracellular RNAses. In addition, sustained siRNA silencing within a cell requires repeated siRNA administrations due to intracellular degradation of these molecules (Gavrilov, *Yale Journal of Biology and Medicine*, 85(2):187 (2012), Whitehead, *Nat Rev Drug Discov*, 8(2):129-38 (2009)). In addition, siRNAs cannot diffuse readily across the cell plasma membrane due to their large size and negative charge. A number of siRNA delivery platforms have been explored, but these platforms are often limited by poor efficacy, high cytotoxicity, or lack of sustained release. To address these limitations, a safe and effective siRNA delivery platform is needed.

Therefore it is an object of the invention to provide an effective, nontoxic, and sustained release delivery system for nucleic acids such as siRNA.

SUMMARY OF THE INVENTION

Polymers including poly(amine-co-ester), poly(amine-co-amide), or a combination thereof, and nanoparticles, particularly solid core nanoparticles, formed therefrom are provided. In some embodiments, the content of a hydrophobic monomer in the polymer is increased relative the content of the same hydrophobic monomer when forming polyplexes in order to form nanoparticles rather than polyplexes.

The polymers can be represented by the general formula:

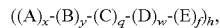

wherein A, B, C, D, and E independently comprise monomeric units derived from lactones, a polyfunctional molecule that contains one or more cations, one or more positively ionizable atoms, or combinations thereof, a diacid or diester, or polyalkylene oxide. The one or more cations are formed from the protonation of a basic nitrogen atom, or from quaternary nitrogen atoms;

wherein the monomeric units comprise at least a lactone, a polyfunctional molecule, and a diacid or diester;

wherein x, y, q, w, and f are independently integers from 0-1000, with the proviso that the sum (x+y+q+w+1) is greater than one;

wherein h is an integer from 1 to 1000; and wherein the percent composition of the lactone is between about 30% and about 100%, calculated as the mole percentage of lactone unit vs. (lactone unit+diester/diacid). Expressed in terms of molar ratio, the lactone vs. (lactone unit+diester/diacid) content is between about 0.3 and about 1. Preferably, the number of ring carbon atoms in the lactone unit is between about 10 and about 24. In some embodiments, the number of carbon atoms in the lactone unit is between about 12 and about 16. In some embodiments, the number of carbon atoms in the lactone unit is 12 (dodecalactone), 15 (pentadecalactone), or 16 (hexadecalactone).

The molecular weight of the lactone unit in the polymer, the lactone unit's content of the polymer, or both, influences the formation of solid core nanoparticles.

For example, the structure of the polymer can be:

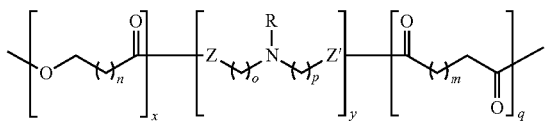

wherein n is an integer from 1-30;

m, o, and p are independently an integer from 1-20;

x, y, and q are independently integers from 1-1000;

Z and Z' are independently O or NR', wherein R and R' are independently hydrogen, substituted or unsubstituted alkyl, or substituted or unsubstituted aryl. Examples of R and R' groups include, but are not limited to, hydrogen, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc. The percent composition of the lactone unit is between about 30% and about 100%, calculated lactone unit vs. (lactone unit+diester/diacid). Expressed in terms of a molar ratio, the lactone unit vs. (lactone unit+diester/diacid) content is between about 0.3 and about 1, i.e., x/(x+q) is between about 0.3 and about 1. Preferably, the number of carbon atoms in the lactone unit is between about 10 and about 24, more preferably the number of carbon atoms in the lactone unit is between about 12 and about 16. Most preferably, the number of carbon atoms in the lactone unit is 12 (dodecalactone), 15 (pentadecalactone), or 16 (hexadecalactone).

Solid core nanoparticles confer the advantage of improved stability of the particles in solution and serum, such as occurs in vivo, relative to non-solid core particles such as particles. The Example below shows that the particles are also particularly well suited for sustained intracellular release of nucleic acid cargos such as siRNA over the course of, for example, two weeks. The particles also show improved siRNA loading compared to traditional PLGA formulations, and reduced cytotoxicity compared to other cationic siRNA delivery platforms with comparable transfection efficiency. In some embodiments, the solid core nanoparticles are fabricated using a double emulsion technique.

Nanoparticles formed of polymers including poly(amine-co-ester), poly(amine-co-amide) have several advantages over nanoparticles formed with hydrophobic polymers. Solid core nanoparticles fabricated from hydrophobic polymers often require the presence of cationic complexing agents to stabilize polynucleotides, particularly negatively charged polynucleotides. Exemplary polynucleotides include, but are not limited to mRNA, DNA vectors, antisense molecules, siRNA, miRNA, aptamers, ribozymes, triplex forming molecules, RNAi, external guide sequences, CRISPR/Cas constructs, etc. As discussed in more detail below, in some embodiments the triplex-forming molecule is a tail clamp peptide nucleic acid (tcPNA). The polynucleotide deliverable by the disclosed particles can be a functional nucleic acid or can be a vector, RNA, or other polynucleotide encoding a functional nucleic acid and designed for expression thereof in cells of interest. The polynucleotide can be single stranded or double stranded.

However, complexing agents are optional in the disclosed formulations because, as discussed in more detail below, the nanoparticles contain cationic amines to stabilize negatively charged nucleic acids and hydrophobic domains to condense the nucleic acid into the core of the formed nanoparticles, thus improving encapsulation efficiency. This increase in nucleic acid loading allows the disclosed solid core nanoparticles to deliver more nucleic acid per cell without increasing total polymer delivered, further reducing cytotoxicity. Cationic delivery platforms are often limited by high cytotoxicity. In comparison, the disclosed nanoparticles offer the advantage of reduced cytotoxicity (low density of cationic amines and high density of hydrophobic domains) and effective nucleic acid transfection. Pharmaceutical compositions including an effective amount of the nanoparticles are also provided, and can be used, for example, for in vitro and in vivo delivery of nucleic acids and other active agents.

Methods of use are also provided. For example, a method of delivering an active agent to cells can include contacting the cells with an effective amount of nanoparticles including the active agent. In some embodiments in which the active agent is a polynucleotide, and a method of transfecting cells includes contacting the cells with an effective amount of the nanoparticles including the polynucleotide. The method of reducing expression of a target gene can include contacting cells expressing the gene with an effective amount of a pharmaceutical composition including nanoparticles with an inhibitory nucleic acid encapsulated, entrapped, embedded, or dispersed therein, or complexed thereto, to reduce expression of the target gene in the cells. The inhibitory nucleic acid can be, for example, an siRNA, miRNA, or a mimic thereof, for example a construct composed of DNA or synthetic nucleotides, but that can have the same molecular weight as RNA. In some embodiments, the polynucleotide is less than 1,000 nucleotides, less than 500 nucleotides, less than 250 nucleotides, less than 100 nucleotides, between about 10 and about 50 nucleotides in length, between about 18 and 28 nucleotides in length, or between about 20 and 25 nucleotides in length. In a particular embodiment, the polynucleotide is 22 nucleotides in length. The polynucleotide can be single-stranded or double-stranded. The contacting can occur in vitro or in vivo. The pharmaceutical composition can be administered to a subject in an effective amount for the inhibitory nucleic acid to reduce one or more disease or disorder symptoms in a subject in need thereof. In some embodiments, reduced expression of the target gene in the subject is sustained for at least 2 week.

BRIEF DESCRIPTION OF THE DRAWINGS

FIG. 1A is a scheme showing the synthesis and chemical structure of a poly(amine-co-ester) (PACE) used in the experiments described in the Example. FIG. 1B is a flow diagram showing double emulsion solvent evaporation-based method of making PACE nanoparticles.

FIG. 2A is a plot showing the loading of siRNA in solid PACE particles compared with standard PLGA & spermidine formulations. FIG. 2B is a curve showing siRNA released from solid PACE over 6 days in phosphate buffered saline at 37° C.

FIGS. 3A-3B are bar graphs showing CIITA/GAPDH (3A) or HLA-DR (3B) mRNA expression levels quantified using qRT-PCR in cultured HUVECs 48 hours after treated with either lipofectamine RNAiMAX or CIITA siRNA nanoparticles for 8 hours. IFN-γ was added to restore MHC class II expression in cultured HUVECs. FIG. 3C is a bar graphs showing HLA-DR protein expression was quantified using flow cytometry after 72 hours.

DETAILED DESCRIPTION OF THE INVENTION

I. Definitions

Figure 4A:
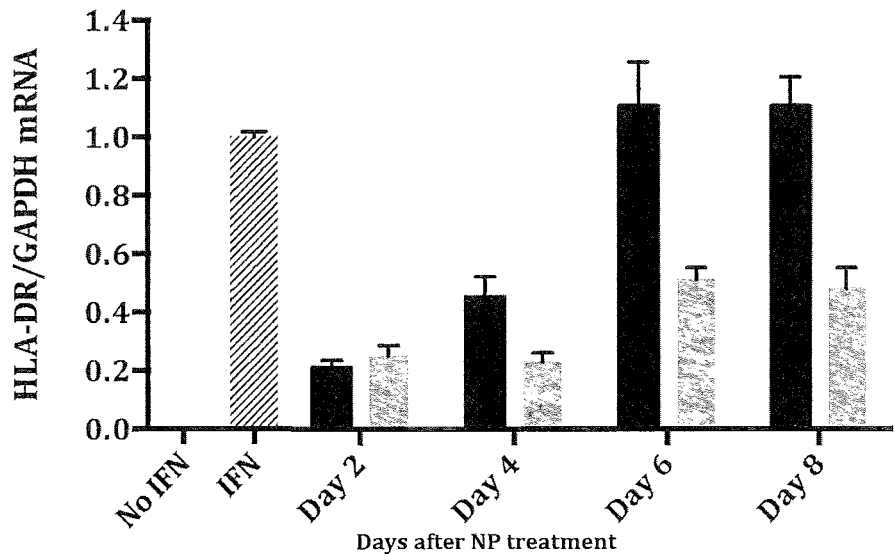
FIGS. 4A and 4B are bar graphs HLA-DR/GAPDH mRNA expression (4A) and HLA-DR mean fluorescence intensity (MFI) normalized to IFN control (4B) in HUVECs treated with CIITA siRNA delivered via Lipofectamine RNAiMAX or PACE NPs for 8 hours and cultured for up to 9 days. Cells were harvested at days 3, 5, 7, and 9, and surface expression of MHC II was quantified using qRT-PCR and flow cytometry.

The terms "lactone" and "lactone unit" are used to describe a chemical compound that includes a cyclic ester, or the open chain chemical structure that results from the cleavage of the ester bond in the cyclic ester. For example, lactone is used to describe the cyclic ester shown below, and the corresponding lactone-derived open chain structure:

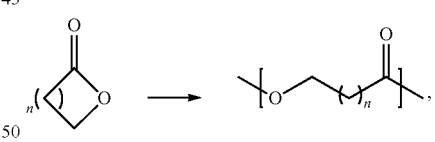

n being an integer. The open chain structure is formed via methods known in the art, including but not limited to, solvolysis, such as hydrolysis, and enzymatic cleavage.

The term "polyplex" as used herein refers to polymeric micro- and/or nanoparticles or micelles having encapsulated therein, dispersed within, and/or associated with the surface of, one or more polynucleotides.

The term "solid core" as relates to "particles" is used to describe a plurality of particles in which the core of each particle contains a matrix that includes one or more materials that are used to form the particles. The particles can be microspheres, microcapsules, microparticles, nanospheres, nanocapsules, and nanoparticles, referred to as solid core microspheres, solid core microcapsules, solid core microparticles, solid core nanospheres, solid core capsules, and solid core nanoparticles, respectively.

The term "microspheres" is art-recognized, and includes substantially spherical colloidal structures, e.g., foamed from biocompatible polymers such as subject compositions, having a size ranging from about one or greater up to about 1000 microns. In general, "microcapsules," also an art-recognized term, may be distinguished from microspheres, because microcapsules are generally covered by a substance of some type, such as a polymeric formulation. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron (1000 nm) in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm. In some embodiments, the average diameter of the particles is from about 200 nm to about 600 nm, preferably from about 200 to about 500 nm. Microparticles can be used for gene therapy, particularly for vaccinations.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10%, 8%, 5%, 3%, or 2% of the median volume diameter.

The term "particle" as used herein refers to any particle formed of, having attached thereon or thereto, or incorporating a therapeutic, diagnostic or prophylactic agent, optionally including one or more polymers, liposomes micelles, or other structural material. A particle may be spherical or nonspherical. A particle may be used, for example, for diagnosing a disease or condition, treating a disease or condition, or preventing a disease or condition.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "diameter" is art-recognized and is used herein to refer to either of the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Sustained release" as used herein refers to release of a substance over an extended period of time in contrast to a bolus type administration in which the entire amount of the substance is made biologically available at one time.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrastemal injection and infusion.

The term "surfactant" as used herein refers to an agent that lowers the surface tension of a liquid.

The term "targeting moiety" as used herein refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. All integer values of the number of backbone carbon atoms between one and 30 are contemplated and disclosed for the straight chain or branched chain alkyls. Likewise, preferred cycloalkyls have from 3-10 carbon atoms in their ring structure, and more preferably have 5, 6, or 7 carbons in the ring structure. All integer values of the number of ring carbon atoms between three and 10 are contemplated and disclosed for the cycloalkyls. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

"Aryl", as used herein, refers to $C_5$-$C_{26}$ aromatic, heterocyclic, fused aromatic, fused heterocyclic, biaromatic, or bihetereocyclic ring systems. Broadly defined, "aryl", as used herein, includes 5-, 6-, 7-, 8-, 9-, 10-, 14, 18, and 24-membered single-ring aromatic groups that may include from zero to four heteroatoms, for example, benzene, naphthalene, anthracene, phenanthrene, chrysene, pyrene, corannulene, coronene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA,* 81:2035-39 (1984), or from another source, binds with high specificity, as described by Chamberlin, et al., *Nature,* 228:227-231 (1970).

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

The term "construct" refers to a recombinant genetic molecule having one or more isolated polynucleotide sequences.

The term "expression control sequence" refers to a nucleic acid sequence that controls and regulates the transcription and/or translation of another nucleic acid sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein "to reprogram a cell" or "cellular reprogramming" means to induce a cell to express one or more polypeptides or functional nucleic acids in an effective amount to change a function of the cell. The function can be any function. For example, an immune cell can be induced to express a receptor which changes the cell's ability to recognize an antigen or to mediate an immune response; or a somatic cell can be induced to express a pluripopency marker(s) which can dedifferentiate the cell from a somatic state to a pluripotent state (i.e., induced pluripotent stem cell (iPS)).

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

A "transgenic organism" as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (2000) Molecular Cloning: A Laboratory Manual, $3^{rd}$ ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanocaldococcus jannaschii, Methanothermobacter thermautotrophicus*, Halobacterium such as *Haloferax volcanii* and Halobacterium species NRC-1, *Archaeoglobus fulgidus, Pyrococcus furiosus, Pyrococcus horikoshii*, and *Aeuropyrum pernix*.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides which do not significantly alter the characteristics of the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences.

"Transformed," "transgenic," "transfected" and "recombinant" refer to a host organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a cell, bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "purified" and like terms relate to the isolation of a molecule or compound in a form that is substantially free (at least 60% free, preferably 75% free, and most preferably 90% free) from other components normally associated with the molecule or compound in a native environment.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

II. Compositions

Polymers including poly(amine-co-ester), poly(amine-co-amide), or a combination thereof, and nanoparticles formed therefrom, particularly solid core nanoparticles are provided. In some embodiments, the content of a hydrophobic monomer in the polymer is increased relative the content of the same hydrophobic monomer when used to form polyplexes. Increasing the content of a hydrophobic monomer in the polymer forms a polymer that can form solid core nanoparticles in the presence of nucleic acids, including RNAs. Unlike polyplexes, these particles are stable for long periods of time during incubation in buffered water, or serum, or upon administration (e.g., injection) into animals. They also provide for a sustained release of nucleic acids (e.g., siRNA) which leads to long term activity (e.g., siRNA mediate-knockdown).

A. Polymers

The polymers have the general formula:

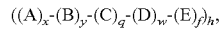

$((A)_x\text{-}(B)_y\text{-}(C)_q\text{-}(D)_w\text{-}(E)_f)_h,$ wherein A, B, C, D, and E independently include monomeric units derived from lactones (such as pentadecalactone), a polyfunctional molecule (such as N-methyldiethanolamine), a diacid or diester (such as diethylsebacate), or polyalkylene oxide (such as polyethylene glycol). In some aspects, the polymers include at least a lactone, a polyfunctional molecule, and a diacid or diester monomeric units. In general, the polyfunctional molecule contains one or more cations, one or more positively ionizable atoms, or combinations thereof. The one or more cations are formed from the protonation of a basic nitrogen atom, or from quaternary nitrogen atoms.

In general, x, y, q, w, and f are independently integers from 0-1000, with the proviso that the sum (x+y+q+w+f) is greater than one. h is an integer from 1 to 1000.

The percent composition of the lactone can be between about 30% and about 100%, calculated as the mole percentage of lactone unit vs. (lactone unit+diester/diacid). Expressed in terms of molar ratio, the lactone unit vs. (lactone unit+diester/diacid) content is between about 0.3 and about 1. Preferably, the number of carbon atoms in the lactone unit is between about 10 and about 24. In some embodiments, the number of carbon atoms in the lactone unit is between about 12 and about 16. In some embodiments, the number of carbon atoms in the lactone unit is 12 (dodecalactone), 15 (pentadecalactone), or 16 (hexadecalactone).

The molecular weight of the lactone unit in the polymer, the lactone unit's content of the polymer, or both, influences the formation of solid core nanoparticles.

Poly(amine-co-ester)s and Poly(amine-co-amides)

a. Polymers

In some embodiments the polymers or nanoparticles formed therefrom, preferably solid core nanoparticles, are made of poly(amine-co-ester)s or poly(amine-co-amides). Suitable polymers are disclosed in WO 2013/082529 and U.S. Pat. No. 9,272,043.

For example, in some embodiments, the polymer has the formula:

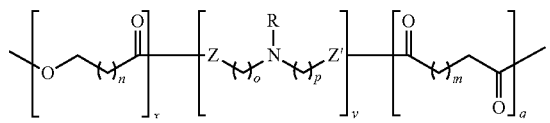

Formula I wherein n is an integer from 1-30, m, o, and p are independently an integer from 1-20, x, y, and q are independently integers from 1-1000, Z and Z' are independently O or NR', wherein R and R' are independently hydrogen, substituted or unsubstituted alkyl, or substituted or unsubstituted aryl. Examples of R and R' groups include, but are not limited to, hydrogen, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc. In particular embodiments, the values of x, y, and q are such that the weight average molecular weight of the polymer is greater than 5,000 Daltons. The polymer can be prepared from one or more lactones, one or more amine-diols, triamines, or hydroxy diamines, and one or more diacids or diesters. In those embodiments where two or more different lactone, diacid or diester, and/or triamine, amine-diol, or hydroxy diamine monomers are used, the values of n, o, p, and/or m can be the same or different.

The percent composition of the lactone unit is between about 30% and about 100%, calculated lactone unit vs. (lactone unit+diester/diacid). Expressed in terms of a molar ratio, the lactone unit vs. (lactone unit +diester/diacid) content is between about 0.3 and about 1, i.e., x/(x+q) is between about 0.3 and about 1. Preferably, the number of carbon atoms in the lactone unit is between about 10 and about 24, more preferably the number of carbon atoms in the lactone unit is between about 12 and about 16. Most preferably, the number of carbon atoms in the lactone unit is 12 (dodecalactone), 15 (pentadecalactone), or 16 (hexadecalactone).

In some embodiments, Z and Z' are O. In some embodiments, Z is O and Z' is NR', or Z is NR' and Z' is O, wherein R' is hydrogen, substituted or unsubstituted alkyl, or substituted or unsubstituted aryl. Examples of R' include, but are not limited to, hydrogen, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

In some embodiments, Z and Z' are O and n is an integer from 1-24, such 4, 10, 13, or 14.

In some embodiments, Z and Z' are O, n is an integer from 1-24, such 4, 10, 13, or 14, and m is an integer from 1-10, such as 4, 5, 6, 7, or 8.

In some embodiments, Z and Z' are O, n is an integer from 1-24, such 4, 10, 13, or 14, m is an integer from 1-10, such as 4, 5, 6, 7, or 8, and o and p are the same integer from 1-6, such 2, 3, or 4.

In some embodiments, Z and Z' are O, n is an integer from 1-24, such 4, 10, 13, or 14, m is an integer from 1-10, such as 4, 5, 6, 7, or 8, and R is alkyl, such as methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, or aryl, such as phenyl, naphthalyl, anthracenyl, phenanthryl, chrysenyl, pyrenyl, tolyl, or xylyl.

In certain embodiments, n is 14 (e.g., pentadecalactone, PDL), m is 7 (e.g., diethylsebacate, DES), o and p are 2 (e.g., N-methyldiethanolamine, MDEA). In certain embodiments, n, m, o, and p are as defined above, and PEG is incorporated as a monomer.

In particular embodiments, the values of x, y, and q are such that the weight average molecular weight of the polymer is greater than 5,000 Daltons.

The polymer can be prepared from one or more substituted or unsubstituted lactones, one or more substituted or unsubstituted amine-diols (Z and Z'=O), triamines (Z and Z'=NR'), or hydroxy-diamines (Z=O, and Z'=NR', or vice versa) and one or more substituted or unsubstituted diacids or diesters. In those embodiments where two or more different lactone, diacid or diester, and/or triamine, amine-diol, or hydroxy diamine monomers are used, than the values of n, o, p, and/or m can be the same or different.

The monomer units can be substituted at one or more positions with one or more substituents. Exemplary substituents include, but are not limited to, alkyl groups, cyclic alkyl groups, alkene groups, cyclic alkene groups, alkynes, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

The polymer is preferably biocompatible. Readily available lactones of various ring sizes are known to possess low toxicity: for example, polyesters prepared from small lactones, such as poly(caprolactone) and poly(p-dioxanone) are commercially available biomaterials which have been used in clinical applications. Large (e.g., $C_{16}$-$C_{24}$) lactones and their polyester derivatives are natural products that have been identified in living organisms, such as bees. Lactones containing ring carbon atoms between 16 and 24 are specifically contemplated and disclosed.

In other embodiments, the polymer is biocompatible and biodegradable. The nucleic acid(s) encapsulated by and/or associated with the particles can be released through different mechanisms, including diffusion and degradation of the polymeric matrix. The rate of release can be controlled by varying the monomer composition of the polymer and thus the rate of degradation. For example, if simple hydrolysis is the primary mechanism of degradation, increasing the hydrophobicity of the polymer may slow the rate of degradation and therefore increase the time period of release. In all case, the polymer composition is selected such that an effective amount of nucleic acid(s) is released to achieve the desired purpose/outcome.

The polymers can further include one or more blocks of an alkylene oxide, such as polyethylene oxide, polypropylene oxide, and/or polyethylene oxide-co-polypropylene oxide. The structure of a PEG-containing polymer is shown below:

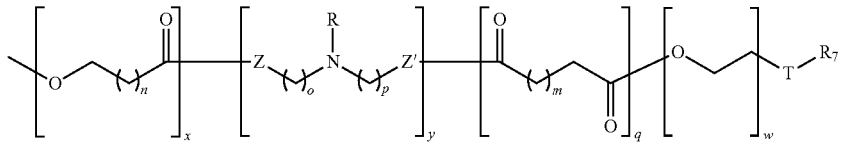

wherein n is an integer from 1-30, m, o, and p are independently an integer from 1-20, x, y, q, and w are independently integers from 1-1000, Z and Z' are independently O or NR', wherein R and R' are independently hydrogen, substituted or unsubstituted alkyl, or substituted or unsubstituted aryl, wherein T is oxygen or is absent, and wherein $R_7$ is hydrogen, alkyl, substituted alkyl, aryl, substituted alkyl, cycloalkyl, substituted cycloalkyl, maleimide, amine, thiol, N-hydroxysuccinimide ester, azide, acrylate, methacrylate, alkyne, hydroxide, or isocynate. In particular embodiments, the values of x, y, q, and w are such that the weight average molecular weight of the polymer is greater than 5,000 Daltons. Examples of R and R' groups include, but are not limited to, hydrogen, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

The structure of a PEG-containing copolymer is shown below:

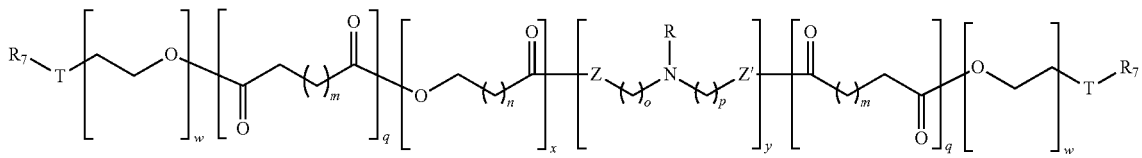

wherein n is an integer from 1-30, m, o, and p are independently an integer from 1-20, x, y, q, and w are independently integers from 1-1000, Z and Z' are independently O or NR', wherein R and R' are independently hydrogen, substituted or unsubstituted alkyl, or substituted or unsubstituted aryl, wherein T is oxygen or is absent, and wherein $R_7$ is hydrogen, alkyl, substituted alkyl, aryl, substituted alkyl, cycloalkyl, substituted cycloalkyl, maleimide, amine, thiol, N-hydroxysuccinimide ester, azide, acrylate, methacrylate, alkyne, hydroxide, or isocynate. In particular embodiments, the values of x, y, q, and w are such that the weight average molecular weight of the polymer is greater than 5,000 Daltons. Examples of R and R' groups include, but are not limited to, hydrogen, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

The blocks of polyalkylene oxide can located at the termini of the polymer (i.e., by reacting PEG having one hydroxy group blocked, for example, with a methoxy group), within the polymer backbone (i.e., neither of the hydroxyl groups are blocked), or combinations thereof.

b. Methods of Making the Polymers

Methods for the synthesis of the polymers from a lactone, a dialkyl ester, and a dialkyl amine using an enzyme catalyst, such as a lipase, are also provided. Exemplary lactones are shown in FIG. 1. In one embodiment, the polymers are prepared as shown in Scheme 1:

Scheme 1: Preparation of poly(amine-co-ester) terpolymers

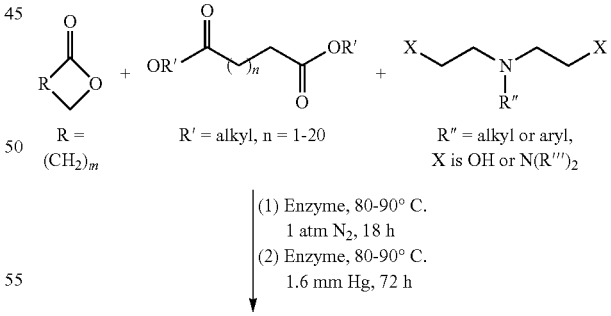

R = $(CH_2)_m$      R' = alkyl, n = 1-20      R" = alkyl or aryl, X is OH or $N(R''')_2$ (1) Enzyme, 80-90° C.
1 atm $N_2$, 18 h
(2) Enzyme, 80-90° C.
1.6 mm Hg, 72 h

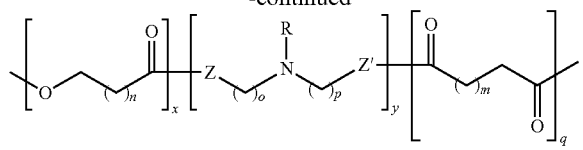

wherein n is an integer from 1-30, m, o, and p are independently an integer from 1-20, and x, y, and q are independently integers from 1-1000. The polymer can be prepared from one or more lactones, one or more amine-diols, tri-amines, or hydroxy diamines, and one or more diacids or diesters. In those embodiments where two or more different lactone, diacid or diester, and/or triamine, amine-diol, or hydroxy diamine monomers are used, than the values of n, o, p, and/or m can be the same or different.

The synthesis of the polymers described herein using PDL, DES, MDA, and PEG as reactants is shown in Scheme 2.

The enzymatic method described herein allows for the synthesis of polymers with diverse chain structures and tunable hydrophobicities. In some embodiments, the hydrophobicity is varied by varying the ring size and/or molar amount of the lactone monomer. Lactone with a wide range of ring sizes (e.g., $C_4$-$C_{24}$, preferably $C_6$-$C_{24}$, more preferably from $C_6$-$C_{16}$) can be used as comonomers. The reaction can be performed in a single step without protection and deprotection of the amino group(s). Such amino-bearing copolyesters are extremely difficult to prepare using conventional organometallic catalysts, as such catalysts are often sensitive to or deactivated by organic amines. These catalysts are also known to be inefficient for polymerizing large lactone ring monomers. Enzymatic catalysts have distinct advantages for producing biomedical polymers owing to the high activity and selectivity of the enzyme and the resulting high purity of products that are metal-free.

Exemplary polymers prepared from a lactone (e.g., caprolactone (CL), co-pentadecalactone (PDL), 16-hexadecanolide (HDL)), diethyl sebacate (DES), and a dialkyl amine

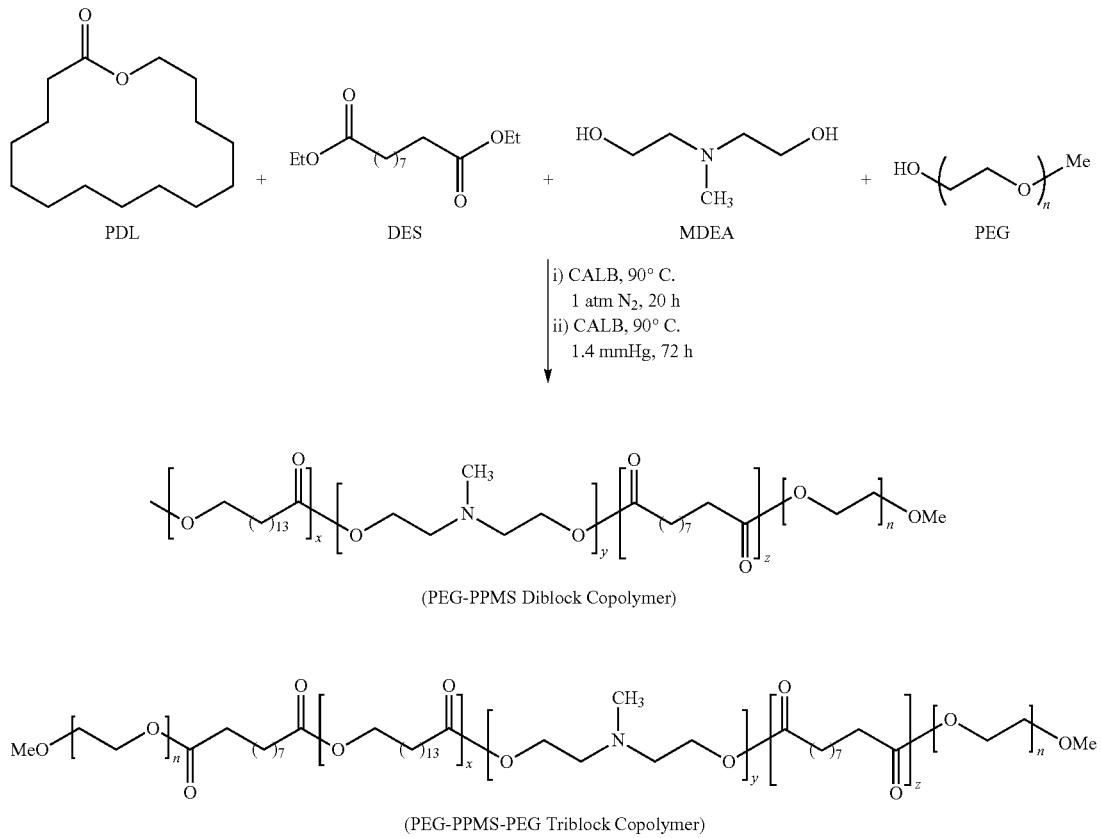

The molar ratio of the monomers (lactone:aminodiol: diester) can vary, for example from about 10:90:90 to about 90:10:10. In some embodiments, the ratio is 10:90:90, 20:80:80, 40:60:60, 60:40:40, or 80:20:20. The weight average molecular weight, as determined by GPC using narrow polydispersity polystyrene standards, can vary for example from about 10,000 Daltons to about 50,000 Daltons, preferably from about 15,000 Daltons to about 50,000 Daltons.

(e.g., N-methyldiethanolamine (MDEA)) are described in Table 1 below. To simplify nomenclature, CL-DES-MDEA, DDL-DES-MDEA, PDL-DES-MDEA, and HDL-DES-MDEA terpolymers are designated as polymer I, II, III, and IV, respectively.

Table 1 shows the yield, composition, weight average molecular weight, polydispersity, and other characterization data of selected terpolymers.

| Name[a] | Lactone/DES/MDEA (Feed) | Lactone/Sebacate/MDEA (Unit Molar Ratio)[b] | Isolated Yield (%) | $M_w$[c] | $M_w/M_n$[c] | Nitrogen Content (wt %) | Solubility in DMSO mg ml$^{-1}$ |
|---|---|---|---|---|---|---|---|
| PMSC[a] | 0:50:50 | 0:50:50 | — | 31800 | 2.3 | 4.9 | >25 |
| I-10% CL[b] | 10:90:90 | 10:90:90 | 85 | 18400 | 1.9 | 4.7 | >25 |
| I-20% CL | 20:80:80 | 20:80:80 | 80 | 19100 | 1.9 | 4.5 | >25 |
| I-40% CL | 40:60:60 | 40:60:60 | 83 | 18400 | 1.8 | 3.9 | >25 |
| I-60% CL | 60:40:40 | 60:40:40 | 81 | 17800 | 1.8 | 3.1 | >25 |
| I-80% CL | 80:20:20 | 80:20:20 | 86 | 20300 | 2.0 | 1.9 | >25 |
| II-10% DDL[c] | 10:90:90 | 10:90:90 | 82 | 24900 | 1.9 | 4.6 | >25 |
| II-20% DDL | 20:80:80 | 20:80:80 | 80 | 29300 | 2.0 | 4.2 | >25 |
| II-40% DDL | 40:60:60 | 40:60:60 | 81 | 25800 | 1.8 | 3.4 | >25 |
| II-60% DDL | 60:40:40 | 60:40:40 | 84 | 47400 | 2.1 | 2.4 | |
| II-80% DDL | 80:20:20 | 80:20:20 | 87 | 40600 | 2.1 | 1.3 | |
| III-10% PDL[d] | 10:90:90 | 10:90:90 | 81 | 30700 | 2.1 | 4.5 | >25 |
| III-20% PDL | 20:80:80 | 20:80:80 | 83 | 38700 | 2.3 | 4.1 | ≈25 |
| III-40% PDL | 40:60:60 | 40:60:60 | 85 | 33300 | 2.1 | 3.1 | |
| III-61% PDL | 60:40:40 | 61:39:39 | 83 | 34500 | 2.3 | 2.1 | |
| III-82% PDL | 80:20:20 | 82:18:18 | 88 | 41700 | 2.7 | 1.0 | |
| IV-10% HDL[e] | 10:90:90 | 10:90:90 | 80 | 25700 | 1.8 | 4.5 | >25 |
| IV-20% HDL | 20:80:80 | 20:80:80 | 81 | 26600 | 1.9 | 4.0 | |
| IV-40% HDL | 40:60:60 | 40:60:60 | 83 | 31200 | 2.2 | 3.1 | |
| IV-61% HDL | 60:40:40 | 61:39:39 | 86 | 37400 | 2.2 | 2.0 | |
| IV-80% HDL | 80:20:20 | 80:20:20 | 89 | 59000 | 2.1 | 1.1 | |

[a]PMSC: poly(N-methyldiethyleneamine sebacate);
[b]CL: caprolactone;
[c]DDL: dodecalactone;
[d]PDL: pentadecalactone;
[e]HDL: hexadecalactone a. The polymer names are abbreviated or simplified. PMSC: poly(N-methyldiethyleneamine sebacate). Polymers I, II, III, and IV represent CL-DES-MDEA, DDL-DES-MDEA, PDL-DES-MDEA, and HDL-DES-MDEA terpolymers, respectively. Each polymer is denoted with x % lactone indicating the lactone unit content [mol % vs. (lactone+sebacate) units] in the polymer.

b. Measured by $^1$H NMR spectroscopy.

c. Measured by GPC using narrow polydispersity polystyrene standards.

B. Therapeutic, Prophylactic or Diagnostic Agents

The polymers described above can be used to prepare micro- and/or nanoparticles having encapsulated therein one or more therapeutic, diagnostic, or prophylactic agents. The agent can be encapsulated within the particle, dispersed within the polymer matrix that forms the particle, covalently or non-covalently associated with the surface of the particle or combinations thereof.

The polymers can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polymer, or to impart properties to the polymer, such as bioadhesion, cell attachment, enhancement of cell growth, inhibition of bacterial growth, and prevention of clot formation.

In preferred embodiments, the agent is a nucleic acid, such as siRNA. However, molecules other than nucleic acids can also be delivered. Since the polymer is very hydrophobic, it can bind with non-charged molecules through hydrophobic forces.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons.

The agent to be delivered can be a small molecule agent (i.e., non-polymeric agent having a molecular weight less than 2,000, 1500, 1,000, 750, or 500 Dalton) or a macromolecule (e.g., an oligomer or polymer) such as proteins, enzymes, peptides, nucleic acids, etc. Suitable small molecule active agents include organic, inorganic, and/or organometallic compounds. The particles can be used for in vivo and/or in vitro delivery of the agent.

Exemplary therapeutic agents that can be incorporated into the particles include, but are not limited to, tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Exemplary diagnostic agents include paramagnetic molecules, fluorescent compounds, magnetic molecules, and radionuclides, x-ray imaging agents, and contrast agents.

1. Polynucleotides

The nanoparticles can include a nucleic acid cargo. The polynucleotide can encode one or more proteins, functional nucleic acids, or combinations thereof. The polynucleotide can be monocistronic or polycistronic. In some embodiments, the polynucleotide is multigenic. In some embodiments, the polynucleotide is transfected into the cell and remains extrachromosomal. In some embodiments, the polynucleotide is introduced into a host cell and is integrated into the host cell's genome. As discussed in more detail below, the compositions can be used in methods of gene therapy. Methods of gene therapy can include the introduction into the cell of a polynucleotide that alters the genotype of the cell. Introduction of the polynucleotide can correct, replace, or otherwise alter the endogenous gene via genetic recombination. Methods can include introduction of an entire replacement copy of a defective gene, a heterologous gene, or a small nucleic acid molecule such as an oligonucleotide. For example, a corrective gene can be introduced into a non-specific location within the host's genome.

In some embodiments, the polynucleotide is incorporated into or part of a vector. Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences and necessary elements for the translation and/or transcription of the inserted coding sequence, which can be, for example, the polynucleotide of interest. The coding sequence can be operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

For example, in some embodiments, the polynucleotide of interest is operably linked to a promoter or other regulatory elements known in the art. Thus, the polynucleotide can be a vector such as an expression vector. The engineering of polynucleotides for expression in a prokaryotic or eukaryotic system may be performed by techniques generally known to those of skill in recombinant expression. An expression vector typically comprises one of the disclosed compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors. It will be appreciated that any of these vectors may be packaged and delivered using the disclosed polymers.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the disclosed compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

a. Polypeptide of Interest

The polynucleotide can encode one or more polypeptides of interest. The polypeptide can be any polypeptide. For example, the polypeptide encoded by the polynucleotide can be a polypeptide that provides a therapeutic or prophylactic effect to an organism or that can be used to diagnose a disease or disorder in an organism. For example, for treatment of cancer, autoimmune disorders, parasitic, viral, bacterial, fungal or other infections, the polynucleotide(s) to be expressed may encode a polypeptide that functions as a ligand or receptor for cells of the immune system, or can function to stimulate or inhibit the immune system of an organism.

In some embodiments, the polynucleotide supplements or replaces a polynucleotide that is defective in the organism.

In some embodiments, the polynucleotide includes a selectable marker, for example, a selectable marker that is effective in a eukaryotic cell, such as a drug resistance selection marker. This selectable marker gene can encode a factor necessary for the survival or growth of transformed host cells grown in a selective culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, the polynucleotide includes a reporter gene. Reporter genes are typically genes that are not present or expressed in the host cell. The reporter gene typically encodes a protein which provides for some phenotypic change or enzymatic property. Examples of such genes are provided in Weising et al. *Ann. Rev. Genetics,* 22, 421 (1988). Preferred reporter genes include glucuronidase (GUS) gene and GFP genes.

b. Functional Nucleic Acids

The polynucleotide can be, or can encode a functional nucleic acid. Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, external guide sequences, CRISPR/Cas constructs, etc. As discussed in more detail below, in some embodiments the triplex-forming molecule is a tail clamp peptide nucleic acid (tcPNA).

The polynucleotide deliverable by the disclosed particles can be a functional nucleic acid or can be a vector, RNA, or other polynucleotide encoding a functional nucleic acid, designed for expression thereof in cells of interest. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

2. Composition of the Polynucleotides

The polynucleotide can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

The polynucleotide can be composed of nucleotide analogs that have been chemically modified to improve stability, half-life, or specificity or affinity for a target sequence, relative to a DNA or RNA counterpart. The chemical modifications include chemical modification of nucleobases, sugar moieties, nucleotide linkages, or combinations thereof. As used herein 'modified nucleotide"or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge. Modifications should not prevent, and preferably enhance, the ability of the oligonucleotides to enter a cell and carry out a function such inhibition of gene expression as discussed above.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

As discussed in more detail below, in one preferred embodiment, the oligonucleotide is a morpholino oligonucleotide.

a. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications

Polynucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O-(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i–1 phosphate in the purine strand of the duplex.

The polynucleotide can be a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation. In some embodiments, oligonucleotides employ morpholino-based subunits bearing base-pairing moieties, joined by uncharged linkages.

c. Internucleotide Linkages

Internucleotide bond refers to a chemical linkage between two nucleoside moieties. Modifications to the phosphate backbone of DNA or RNA oligonucleotides may increase the binding affinity or stability polynucleotides, or reduce the susceptibility of polynucleotides to nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, et al., Organic Chem., 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA. Methods for the chemical assembly of PNAs are well known. See, for example, U.S. Pat. Nos. 5,539,082, 5,527,675, 5,623,049, 5,714,331, 5,736,336, 5,773,571, and 5,786,571.

Polynucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. For example, lysine and arginine residues can be added to a bis-PNA linker or can be added to the carboxy or the N-terminus of a PNA strand. Polynucleotides may further be modified to be end capped to prevent degradation using a 3' propylamine group. Procedures for 3' or 5' capping oligonucleotides are well known in the art.

C. Targeting Moieties

In some embodiments, the particles include a cell-type or cell-state specific targeting domain or targeting signal. Examples of moieties which may be linked or unlinked to the particles include, for example, targeting moieties which provide for the delivery of molecules to specific cells. The targeting signal or sequence can be specific for a host, tissue, organ, cell, organelle, non-nuclear organelle, or cellular compartment. For example, the compositions disclosed herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions disclosed here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

The targeting moiety can be an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

One skilled in the art will appreciate that the tropism of the particles described can be altered by merely changing the targeting signal. It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

Tumor Targeting

In one embodiment, the targeting signal is used to selectively target tumor cells. Tumor cells express cell surface markers which may only be expressed in the tumor or present in non-tumor cells but preferentially presented in tumor cells. Such markers can be targeted to increase delivery of the particles to cancer cells.

For example, in some embodiments, the targeting moiety is a polypeptide including an arginine-glycine-aspartic acid sequence. For example, the targeting moiety can be an arginine-glycine-aspartic acid-lysine (RGDK, mRGD) other polypeptide that includes the RGD sequence and is capable of binding to tumor endothelium through the interaction of RGD with $\alpha_v\beta_3$ and $\alpha_v\beta_5$. In some embodiments, a targeting moiety includes the polypeptide sequence R/KxxR/K, where "x" is any amino acid, and which allows binding to neuropilin-1. Binding with integrins or neuropilin-1 are two approaches for improving tumor-targeted and tissue-penetrating delivery to tumors in vivo. Similar approaches have been reported to facilitate ligand-specific gene delivery in vitro and targeted gene delivery to liver, spleen, and bone marrow in vivo.

Other, exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, NCAM, EGFR, CD44, and folate receptor. In one embodiment, the targeting signal consists of antibodies which are specific to the tumor cell surface markers.

Antibodies

Another embodiment provides an antibody or antigen binding fragment thereof bound to the disclosed particle acts as the targeting signal. The antibodies or antigen binding fragment thereof are useful for directing the particle to a cell type or cell state. In one embodiment, the particle is coated with a polypeptide that is an antibody binding domain, for example from a protein known to bind antibodies such as Protein A and Protein G from *Staphylococcus aureus*. Other domains known to bind antibodies are known in the art and can be substituted. The antibody binding domain links the antibody, or antigen binding fragment thereof, to the particle.

In certain embodiments, the antibody that serves as the targeting signal is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting signal includes all or part of an antibody that directs the particle to the desired target cell type or cell state. Antibodies can be monoclonal or polyclonal, but are preferably monoclonal. For human gene therapy purposes, antibodies can be derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Brain Targeting

In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells Exemplary markers specific for these cell types and states are well known in the art and include, but are not limited to CD133 and Neurosphere.

Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine.

In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7, and MR4.

III. Methods of Preparing Nanoparticles

Although polyplexes are very effective as nontoxic transfection agents, they do not form stable particles. Methods of making stable nanoparticles using the disclosed polymers are provided. In preferred embodiments, the particles are loaded with nucleic acid cargo such as siRNA for delivery to cell in vitro, ex vivo, or in vivo.

In some embodiments, the content of a hydrophobic monomer in the polymer is increased relative the content of the same hydrophobic monomer when forming polyplexes. Increasing the content of a hydrophobic monomer in the polymer forms a polymer that can form solid core nanoparticles in the presence of nucleic acids. Unlike polyplexes, these particles are stable for long periods of time during incubation in buffered water, or serum, or upon administration (e.g., injection) into animals. They also provide for a sustained release of nucleic acids (e.g., siRNA) which leads to long term activity (e.g., siRNA mediate-knockdown).

For example, in some embodiments, the content of PDL is increased in the polymer relative to the other monomers. For instance, to form solid core particle the lactone unit's content is between about 30% and about 100%, calculated as the mole percentage of lactone unit vs (lactone unit+diester/diacid). Expressed in terms of a molar ratio, the lactone unit vs. (lactone unit+diester/diacid) content is between about 0.3 and about 1. The feed molar content of the polyfunctional compound, such as diethanolamine can be varied as well. Examples of feed molar ratios include, but are not limited to, 40:60:60, 50:50:50, 60:40:40, 70:30:30, 80:20:20, and 90:10:10, for the lactone unit:diacid/diester:polyfunctional molecule.

In some embodiments, solid core nanoparticles are fabricated using the double-emulsion solvent evaporation technique. A suitable double-emulsion technique is exemplified in the Example below. Nucleic acid in buffer (e.g. sodium acetate buffer pH 5.2) is added to polymer dissolved in a solvent such as methylene chloride and sonicated to form the first emulsion. Next, the emulsion is added to a solution containing a surfactant (e.g., 5% PVA solution) and sonicated to form the second emulsion. The final emulsion is then poured into a solution containing the surfactant in an aqueous solution (e.g., 0.3% PVA solution) and stirred for a period of time to allow the dichloromethane to evaporate and the particles to harden, and lyophilized. The concentration of the surfactant used to form the emulsion, and the sonication time and amplitude can been optimized according to principles known in the art for formulating particles with a desired diameter. The particles can be collected by centrifugation. If it is desirable to store the nanoparticles for later use, they can be rapidly frozen, and lyophilized.

Double-emulsion solvent evaporation techniques are also disclosed in U.S. Published Application No. 2011/0008451 and U.S. Published Application No. 2011/0268810, Fahmy, et al., *Biomaterials*, 26:5727-5736, (2005), and McNeer, et al., *Mol. Ther.* 19, 172-180 (2011)). The nucleic acids or nucleic acid/polycation complexes can be reconstituted in an aqueous solution. Nucleic acid and polycation amounts are discussed in more detail below and can be chosen, for example, based on amounts and ratios disclosed in U.S. Published Application No. 2011/0008451 or U.S. Published Application No. 2011/0268810, or used by McNeer, et al., (McNeer, et al., *Mol. Ther.* 19, 172-180 (2011)), or by Woodrow et al. for small interfering RNA encapsulation (Woodrow, et al., *Nat Mater*, 8:526-533 (2009)). This aqueous solution is then added dropwise to a polymer solution of a desired polymer dissolved in an organic solvent to form the first emulsion.

Additional techniques for encapsulating the nucleic acid and polycation complex into polymeric nanoparticles are described below.

A. Solvent Evaporation

In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid particles. The resulting particles are washed with water and dried overnight in a lyophilizer. Particles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

B. Solvent Evaporation Microencapsulation

In solvent evaporation microencapsulation, the polymer is typically dissolved in a water immiscible organic solvent and the material to be encapsulated is added to the polymer solution as a suspension or solution in an organic solvent. An emulsion is formed by adding this suspension or solution to a beaker of vigorously stirring water (often containing a surface active agent, for example, polyethylene glycol or polyvinyl alcohol, to stabilize the emulsion). The organic solvent is evaporated while continuing to stir. Evaporation results in precipitation of the polymer, forming solid microcapsules containing core material.

The solvent evaporation process can be used to entrap a liquid core material in a polymer such as PLA, PLA/PGA copolymer, or PLA/PCL copolymer microcapsules. The polymer or copolymer is dissolved in a miscible mixture of solvent and nonsolvent, at a nonsolvent concentration which is immediately below the concentration which would produce phase separation (i.e., cloud point). The liquid core material is added to the solution while agitating to form an emulsion and disperse the material as droplets. Solvent and nonsolvent are vaporized, with the solvent being vaporized at a faster rate, causing the polymer or copolymer to phase separate and migrate towards the surface of the core material droplets. This phase-separated solution is then transferred into an agitated volume of nonsolvent, causing any remaining dissolved polymer or copolymer to precipitate and extracting any residual solvent from the formed membrane. The result is a microcapsule composed of polymer or copolymer shell with a core of liquid material.

Solvent evaporation microencapsulation can result in the stabilization of insoluble active agent particles in a polymeric solution for a period of time ranging from 0.5 hours to several months. Stabilizing an insoluble pigment and polymer within the dispersed phase (typically a volatile organic solvent) can be useful for most methods of microencapsulation that are dependent on a dispersed phase, including film casting, solvent evaporation, solvent removal, spray drying, phase inversion, and many others.

The stabilization of insoluble active agent particles within the polymeric solution could be critical during scale-up. By stabilizing suspended active agent particles within the dispersed phase, the particles can remain homogeneously dispersed throughout the polymeric solution as well as the resulting polymer matrix that forms during the process of microencapsulation.

Solvent evaporation microencapsulation (SEM) have several advantages. SEM allows for the determination of the best polymer-solvent-insoluble particle mixture that will aid in the formation of a homogeneous suspension that can be used to encapsulate the particles. SEM stabilizes the insoluble particles or pigments within the polymeric solution, which will help during scale-up because one will be able to let suspensions of insoluble particles or pigments sit for long periods of time, making the process less time-dependent and less labor intensive. SEM allows for the creation of nanoparticles that have a more optimized release of the encapsulated material.

C. Solvent Removal Microencapsulation

In solvent removal microencapsulation, the polymer is typically dissolved in an oil miscible organic solvent and the material to be encapsulated is added to the polymer solution as a suspension or solution in organic solvent. Surface active agents can be added to improve the dispersion of the material to be encapsulated. An emulsion is formed by adding this suspension or solution to vigorously stirring oil, in which the oil is a nonsolvent for the polymer and the polymer/solvent solution is immiscible in the oil. The organic solvent is removed by diffusion into the oil phase while continuing to stir. Solvent removal results in precipitation of the polymer, forming solid microcapsules containing core material.

D. Spontaneous Emulsification

Spontaneous emulsification involves solidifying emulsified liquid polymer droplets by changing temperature, evaporating solvent, or adding chemical cross-linking agents. The physical and chemical properties of the encapsulant, and the material to be encapsulated, dictates the suitable methods of encapsulation. Factors such as hydrophobicity, molecular weight, chemical stability, and thermal stability affect encapsulation.

E. Solvent Removal

This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make particles from polymers with high melting points and different molecular weights. Particles that range between 1-300 microns can be obtained by this procedure. The external morphology of spheres produced with this technique is highly dependent on the type of polymer used.

F. Nanoprecipitation

In nanoprecipitation, the polymer and nucleic acids are co-dissolved in a selected, water-miscible solvent, for example DMSO, acetone, ethanol, acetone, etc. In a preferred embodiment, nucleic acids and polymer are dissolved in DMSO. The solvent containing the polymer and nucleic acids is then drop-wise added to an excess volume of stirring aqueous phase containing a stabilizer (e.g., poloxamer, PLURONIC®, and other stabilizers known in the art). Particles are formed and precipitated during solvent evaporation. To reduce the loss of polymer, the viscosity of the aqueous phase can be increased by using a higher concentration of the stabilizer or other thickening agents such as glycerol and others known in the art. Lastly, the entire dispersed system is centrifuged, and the nucleic acid-loaded polymer nanoparticles are collected and optionally filtered. Nanoprecipitation-based techniques are discussed in, for example, U.S. Pat. No. 5,118,528.

Advantages to nanoprecipitation include: the method can significantly increase the encapsulation efficiency of drugs that are polar yet water-insoluble, compared to single or double emulsion methods (Alshamsan, *Saudi Pharmaceutical Journal*, 22(3):219-222 (2014)). No emulsification or high shear force step (e.g., sonication or high-speed homogenization) is involved in nanoprecipitation, therefore preserving the conformation of nucleic acids. Nanoprecipitation relies on the differences in the interfacial tension between the solvent and the nonsolvent, rather than shear stress, to produce nanoparticles. Hydrophobicity of the drug will retain it in the instantly-precipitating nanoparticles; the un-precipitated polymer due to equilibrium is "lost" and not in the precipitated nanoparticle form.

Polycations

In some embodiments, the nucleic acid is first complexed to a polycation. Complexation can be achieved by mixing the nucleic acids and polycations at an appropriate molar ratio. When a polyamine is used as the polycation species, it is useful to determine the molar ratio of the polyamine nitrogen to the polynucleotide phosphate (N/P ratio). In a preferred embodiment, nucleic acids and polyamines are mixed together to form a complex at an N/P ratio of between approximately 8:1 to 15:1. The volume of polyamine solution required to achieve particular molar ratios can be determined according to the following formula:

$$V_{NH2} = \frac{C_{nucacid,final} \times M_{w,nucacid}/C_{nucacid,final} \times M_{w,P} \times \Phi_{N:P} \times \Phi V_{final}}{C_{NH2}/M_{w,NH2}}$$

where $M_{w,nucacid}$=molecular weight of nucleic acid, $M_{w,P}$=molecular weight of phosphate groups of the nucleic acid, $\Phi_{N:P}$=N:P ratio (molar ratio of nitrogens from polyamine to the ratio of phosphates from the nucleic acid), $C_{NH2}$, stock=concentration of polyamine stock solution, and $M_{w,NH2}$=molecular weight per nitrogen of polyamine.

Polycation complexation with nucleic acids can be achieved by mixing solutions containing polycations with solutions containing nucleic acids. The mixing can occur at any appropriate temperature. In one embodiment, the mixing occurs at room temperature. The mixing can occur with mild agitation, such as can be achieved through the use of a rotary shaker Methods of mixing polynucleotides with polycations to condense the polynucleotide are known in the art. See for example U.S. Published Application No. 2011/0008451.

The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values. Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quartemized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In some embodiments, the polycation is a polyamine Polyamines are compounds having two or more primary amine groups. Suitable naturally occurring polyamines include, but are not limited to, spermine, spermidine, cadaverine and putrescine. In a preferred embodiment, the polyamine is spermidine.

In another embodiment, the polycation is a cyclic polyamine. Cyclic polyamines are known in the art and are described, for example, in U.S. Pat. No. 5,698,546, WO 1993/012096 and WO 2002/010142. Exemplary cyclic polyamines include, but are not limited to, cyclen.

Spermine and spermidine are derivatives of putrescine (1,4-diaminobutane) which is produced from L-ornithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from S-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

IV. Methods of Using the Particles

A. Drug Delivery

The particles described herein can be used to deliver an effective amount of one or more therapeutic, diagnostic, and/or prophylactic agents to a patient in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The particles may be administered as a dry powder, as an aqueous suspension (in water, saline, buffered saline, etc.), in a hydrogel, organogel, or liposome, in capsules, tablets, troches, or other standard pharmaceutical excipient.

Exemplary cells, tissue, and organs treatable with the disclosed compositions include, but are not limited to, brain, lung, liver, spleen, blood vessels, and tumors. The particles can be contacted with the cells, tissue, or organs in vitro, ex vivo, or in vivo.

B. Transfection

The disclosed compositions can be used in a method of delivering polynucleotides to cells, organs or tissue. For example, the particles can be used for transfection of cells, which can occur in vitro, ex vivo, or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000 or polyethylenimine (PEI).

1. Cells

The methods typically involve contacting the cells with particles including a polynucleotide in an effective amount to introduce the polynucleotide into the cell's cytoplasm. In some embodiments, the polynucleotide is delivered to the cell in an effective amount to change the genotype or a phenotype of the cell. The cells can be primary cells isolated from a subject, or cells of an established cell line. The cells can be of a homogenous cell type, or can be a heterogeneous mixture of different cells types. For example, the particles can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture. Exemplary cell lines are those available from American Type Culture Collection including tumor cell lines.

Any eukaryotic cell can be transfected to produce cells that express a specific nucleic acid, for example a metabolic gene, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. In another embodiment, siRNA, antisense polynucleotides (including siRNA or antisense polynucleotides) or inhibitory RNA can be transfected into a cell using the compositions described herein.

The methods are particularly useful in the field of personalized therapy, for example, to repair a defective gene, de-differentiate cells, or reprogram cells. For example, target cells are first isolated from a donor using methods known in the art, contacted with the particles including a polynucleotide causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro to repair, de-differentiate, re-differentiate, and/or re-program the cell. The cells can be monitored, and the desired cell type can be selected for therapeutic administration.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-teen, for later use. In one embodiment, fibroblasts, keratinocytes or hematopoietic stem cells are isolated from a patient and repaired, de-differentiated, or reprogrammed in vitro to provide therapeutic cells for the patient.

2. Polynucleotides

The particular polynucleotide delivered by the particles can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination.

In some embodiments, the polynucleotide encodes a protein. Exemplary proteins include, for example, (a) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor-α, hepatocyte growth factor and insulin-like growth factor; (b) cell cycle inhibitors such as cyclin-dependent kinases, thymidine kinase ("TK"), and other agents useful for interfering with cell proliferation; (c) bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. BMPs are typically dimeric proteins that can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the particles are used to deliver mRNA or non-integrating expression vectors that are expressed transiently in the host cell.

In a preferred embodiment, the polynucleotide is a pro-apoptotic construct, for example an expression vector encoding TNF-related apoptosis-inducing ligand (TRAIL), which is targeted to tumor cells.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No.2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule.

The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased target site flexibility over methods of induced recombination such as triple-helix oligonucleotides and bis-peptide nucleic acids which require a polypurine sequence in the target double-stranded DNA.

Another method is CRISPR/Cas. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science*, 15:339(6121):819-823 (2013) and Jinek, et al., *Science*, 337(6096):816-21 (2012)). By transfecting a cell with the required elements including a cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and faun a chimeric crRNA-tracrRNA hybrid where a mature crRNA is fused to a partial tracrRNA via a synthetic stem loop to mimic the natural crRNA:tracrRNA duplex as described in Cong, *Science*, 15:339(6121):819-823 (2013) and Jinek, et al., *Science*, 337(6096):816-21 (2012)). A single fused crRNA-tracrRNA construct can also be referred to as a guide RNA or gRNA (or single-guide RNA (sgRNA)). Within an sgRNA, the crRNA portion can be identified as the "target sequence" and the tracrRNA is often referred to as the "scaffold."

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites. While the specifics can be varied in different engineered CRISPR systems, the overall methodology is similar. A practitioner interested in using CRISPR technology to target a DNA sequence (such as CTPS1) can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

B. Transplantation

The compositions are useful in various methods of transplantation. In some embodiments, transplantable material, for example, cells, tissues, organs, limbs, digits or a portion of the body, preferably the human body, are contacted with the particles generally as discussed above. The transplants can be allogenic or xenogenic. In some embodiments, the particles are administered to a site of transplantation prior to, at the time of, or following transplantation. For example, the particles can be administered to a site of transplantation parenterally, such as by subcutaneous injection.

In other embodiments, the particles are administered ex vivo directly to cells, tissue or organ to be transplanted. In one embodiment, the transplant material is contacted with particles prior to transplantation, after transplantation, or both.

In other embodiments, particles are administered to immune tissues or organs, such as lymph nodes or the spleen.

The transplant material can be modified prior to transplant. For example, the transplant material can be genetically modified to express a protein that aids in the inhibition or reduction of transplant rejection.

The transplant material can be treated with enzymes or other materials that remove cell surface proteins, carbohydrates, or lipids that are known or suspected in being involved with immune responses such as transplant reject 1. Cells Populations of any types of cells can be transplanted into a subject. The cells can be homogenous or heterogenous. Heterogeneous means the cell population contains more than one type of cell. Exemplary cells include progenitor cells such as stem cells and pluripotent cells which can be harvested from a donor and transplanted into a subject. The cells are optionally treated prior to transplantation as mention above. Such treatment includes transfecting the cells ex vivo with a nucleic acid construct enabling the cells to express B7-H4 polypeptides or fragments, or fusions thereof in vitro and in vivo. Methods for transfecting cells are well known in the art.

Ex vivo methods of nucleic acid delivery can include, for example, the steps of harvesting cells from a subject, culturing the cells, transducing them with an expression vector, and maintaining the cells under conditions suitable for expression of the encoded polypeptides. These methods are known in the art of molecular biology. An exemplary nucleic acid vector includes but is not limited to an adenoviral vector. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. Other exemplary cells that can be transplanted include, but are not limited to, islet cells, hematopoietic cells, muscle cells, cardiac cells, neural cells, embryonic stem cells, adult stem cells, T cells, lymphocytes, dermal cells, mesoderm, endoderm, and ectoderm cells.

2. Tissues

Any tissue can be used as a transplant. Exemplary tissues include skin, adipose tissue, cardiovascular tissue such as veins, arteries, capillaries, valves; neural tissue, bone marrow, pulmonary tissue, ocular tissue such as corneas and lens, cartilage, bone, and mucosal tissue. The tissue can be modified as discussed above.

3. Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of particles to inhibit or reduce chronic transplant rejection relative to a control.

C. In Vivo Methods

The disclosed compositions can be used in a method of delivering polynucleotides to cells in vivo. The disclosed nanoparticles are more efficient and/or less toxic for transfection of polynucleotides than alternative transfection reagents includes LIPOFECTAMINE 2000, PEI, and even other PMSCs. Accordingly, in some embodiments, the cell specific particles including a therapeutic polynucleotide are administered systemically in vivo to a treat a disease, for example cancer.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

1. Pharmaceutical Compositions

Pharmaceutical compositions including nucleic acids and, optionally, polypeptides are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the particles to the immediate area of the implant.

The particles can be provided to the cell either directly, such as by contacting it with the cell, or indirectly, such as through the action of any biological process. For example, the particles can be formulated in a physiologically acceptable carrier or vehicle, and injected into a tissue or fluid surrounding the cell. The particles can cross the cell membrane by simple diffusion, endocytosis, or by any active or passive transport mechanism.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the particle-associated nucleic acid administered to an individual will be less than the amount of the unassociated nucleic acid that must be administered for the same desired or intended effect.

2. Formulations for Parenteral Administration

In a preferred embodiment the particles are administered in an aqueous solution, by parenteral injection. As discussed in the Examples below, in some embodiments, a formulation suitable for systemic administration by injection includes glucose.

The formulation can be in the form of a suspension or emulsion. In general, pharmaceutical compositions are provided including effective amounts of nucleic acids optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

3. Formulations for Topical and Mucosal Administration

The particles can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the ULTRAVENT® nebulizer (Mallinckrodt Inc., St. Louis, Mo.); the ACORN® II nebulizer (Marquest Medical Products, Englewood, Colo.); the VENTOLIN® metered dose inhaler (Glaxo Inc., Research Triangle Park, N.C.); and the SPINHALER® powder inhaler (Fisons Corp., Bedford, Mass.). Nektar, Alketmes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets, capsules, or lozenges.

Transdermal formulations may also be prepared. These will typically be ointments, lotions, sprays, or patches, all of which can be prepared using standard technology. Transdermal formulations can include penetration enhancers.

4. Co-Administration

Particles disclosed herein can optionally be co-administered with one or more additional active agents. Co-administration can include the simultaneous and/or sequential administration of the one or more additional active agents and the particles. The one or more additional active agents and the particles can be included in the same or different pharmaceutical formulation. The one or more additional active agents and the particles can achieve the same or different clinical benefit. An appropriate time course for sequential administration may be chosen by the physician, according to such factors as the nature of a patient's illness, and the patient's condition. In certain embodiments, sequential administration includes the co-administration of one or more additional active agents and the nanoparticle gene carriers within a period of one week, 72 hours, 48 hours, 24 hours, or 12 hours.

The additional active agent can be chosen by the user based on the condition or disease to be treated. Example of additional active agents include, but are not limited to, vitamin supplements, nutritional supplements, anti-anxiety medication, anti-depression medication, anti-coagulants, clotting factors, anti-inflammatories, steroids such as corticosteroids, analgesic, etc.

If the disease to be treated is cancer, the particles can be administered to a subject in combination with a chemotherapeutic regime, a radiological treatment, a surgical intervention, or combinations thereof. For example, in some methods, the particles are co-administered with a chemotherapeutic drug or immunostimulatory drug. The disclosed compositions can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; CekS; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

Other agents that can be administered in combination with particles include PD-1 antagonists such as an anti-B7-H1 antibody or an anti-PD-1 antibody, an anti-CTLA4 antibody, a mitosis inhibitor, such as paclitaxel, an aromatase inhibitor, such as letrozole, an A2AR antagonist, an angiogenesis inhibitor, anthracyclines, oxaliplatin, doxorubicin, TLR4 antagonists, and IL-18 antagonists.

D. Diseases to be Treated

Embodiments of the present disclosure provide compositions and methods applicable for gene therapy protocols and the treatment of gene related diseases or disorders. Cell dysfunction can also be treated or reduced using the disclosed compositions and methods. In some embodiments, diseases amenable to gene therapy are specifically targeted. The disease can be in children, for example individuals less than 18 years of age, typically less than 12 years of age, or adults, for example individuals 18 years of age or more. Thus, embodiments of the present disclosure are directed to treating a host diagnosed with a disease, by transfection of the particle including a polynucleotide into the cell affected by the disease and wherein the polynucleotide encodes a therapeutic protein. In another embodiment, an inhibitory RNA is directed to a specific cell type or state to reduce or eliminate the expression of a protein, thereby achieving a therapeutic effect. The present disclosure encompasses manipulating, augmenting or replacing genes to treat diseases caused by genetic defects or abnormalities.

Suitable genetic based diseases that can be treated with the compositions disclosed herein include but are not limited to:

Mitochondrial Disease: Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy;MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Ophthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Ophthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Nuclear Disease: Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebellar atrophy, Williams syndrome, Ataxia telangiectasia, Anemia, sickle cell, Burkitt lymphoma, Gaucher disease, Hemophilia, Leukemia, Paroxysmal nocturnal hemoglobinuria, Porphyria, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.

Infectious Disease: Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers: Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders: Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, Porphyria, Refsum disease, Tangier disease, Wilson's disease, Zellweger syndrome, progerias, SCID.

Autoimmune Disorders: Autoimmune polyglandular syndrome, lupus, type I diabetes, scleroderma, multiple sclerosis, Crohn's disease, chronic active hepatitis, rheumatoid arthritis, Graves' disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders: Alopecia, Diastrophic dysplasia, Ellis-van Creveld syndrome, Asthma, Arthritis, including osteoarthritis, rheumatoid arthritis, and spondyloarthropathies.

Age-Related Disorders: Alzheimer Disease, Parkinson's Disease, Atherosclerosis, Age-Related Macular Degeneration, Age-related Osteoporosis.

The disclosed methods and compositions can also be used to treat, manage, or reduce symptoms associated with aging, in tissue regeneration/regenerative medicine, stem cell transplantation, inducing reversible genetic modifications, expressing inhibitory RNA, cognitive enhancement, performance enhancement, and cosmetic alterations to human or non-human animal.

EXAMPLE

Example

PACE NPs Effectively Silence siRNA Expression in HUVECs In Vitro

Materials and Methods

Poly(amine)-co-ester (PACE) nanoparticles were fabricated using a double-emulsion solvent evaporation technique (FIGS. 1A-1B). The nanoparticles were generated using the PACE polymers shown in Table 1 above. siRNA in sodium acetate buffer was added to PACE dissolved in methylene chloride and sonicated to form the first emulsion. Next, the emulsion was added to a 5% PVA solution and sonicated to form the second emulsion. The particles were hardened in 0.3% PVA solution for 15 mins with a rotavapor and lyophilized for 48 hours with or without the addition of trehalose.

Post fabrication, nanoparticle morphology and size were characterized using scanning electron microscopy.

siRNA loading and release were quantified using Quant-iT PicoGreen.

Knockdown via CIITA siRNA loaded nanoparticles is evaluated in human umbilical vein endothelial cells (HUVECs) in vitro. Endothelial cells are treated with IFN-γ to restore in vivo MHC II expression that is lost in endothelial cell culture.

Results

Solid, spherical nanoparticles encapsulating siRNA were fabricated using PACE with 70% lactone content. These particles demonstrated significantly improved siRNA loading (490 pmol/mg) compared to traditional formulations of PLGA nanoparticles complexed with polycationic spermidine (95 pmol/mg) (FIG. 2A), sustained siRNA release over 6 days during incubation in phosphate buffered saline at 37° C. (FIG. 2B), and effective internalization by endothelial cells.

Figure 4B:
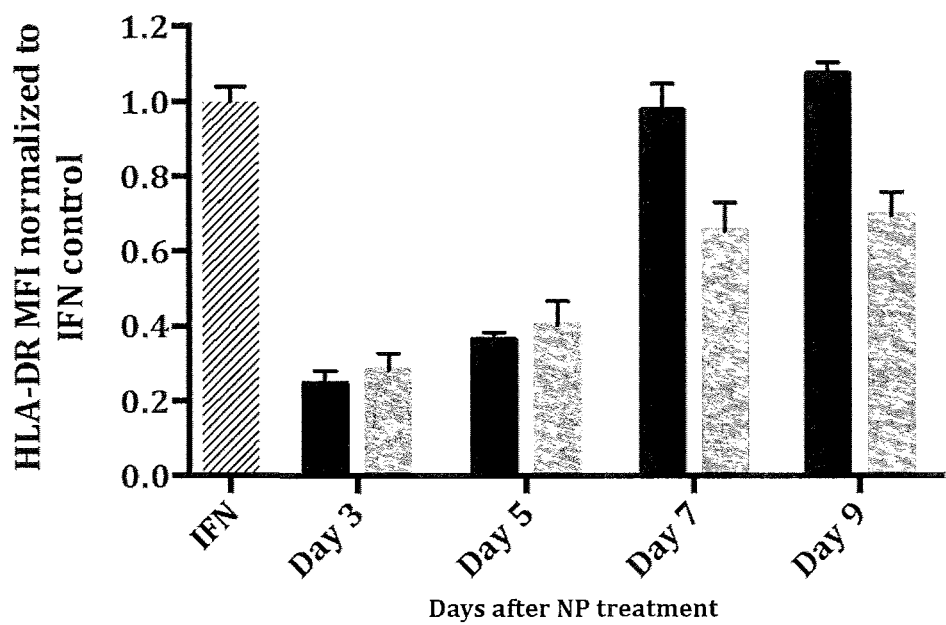

A reduction in MHC class II (HLA-DR) mRNA and protein expression in cells transfected with NPs was observed (FIGS. 3A-3B). Cells treated with PACE NPs were also as effective as lipofectamine for 3 day knockdown, and demonstrated prolonged MHC II knockdown compared to those treated with lipofectamine at 7 and 9 days after treatment (FIGS. 4A and 4B).

These experiments illustrate that poly(amine-co-ester) (PACE)—can be used to produce nanoparticles that can encapsulate nucleic acids such as siRNA. The siRNA-loaded nanoparticles provide sustained gene silencing to endothelial cells in vitro. The results show significant knockdown of CIITA, which leads to reduction in MHC class II expression, in endothelial cells treated with nanoparticles loaded with CIITA siRNA. In addition, surface expression of MHC II on these endothelial cells, as detected by flow cytometry, was reduced for over 9 days.

In summary, these experiments illustrate the fabrication of solid core nanoparticles using biodegradable poly(amine-co-ester) and their use for delivery of siRNA therapeutics. The particles demonstrate dramatically improved siRNA loading (>80% of starting siRNA encapsulated into nanoparticles) compared to traditional degradable polymer nanoparticle formulations (FIG. 2A). In addition, when tested in hard-to-transfect endothelial cells, the nanoparticles demonstrated significantly reduced cytotoxicity and prolonged duration of silencing (>9 days) compared to commercial lipofectamine RNAiMAX (FIGS. 3A-3C and 4A-4B). Furthermore, nanoparticle properties, such as zeta potential, size, release profile, and selectivity for specific organs/tissues in vivo can be tuned by changing the percent composition of 15-pentadecanolide in the polymer.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A solid polymeric nanoparticle comprising a polymer having the general formula:

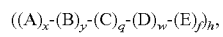

wherein A, B, C, D, and E are independently a lactone unit, a polyfunctional molecule comprising one or more cations, one or more positively ionizable atoms, or combinations thereof, a diacid or diester, or polyalkylene oxide;

wherein at least one lactone unit is

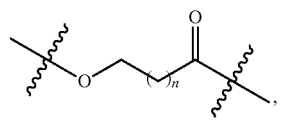

wherein at least one polyfunctional molecule is

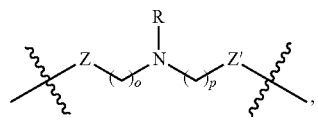

wherein at least one diacid or diester is

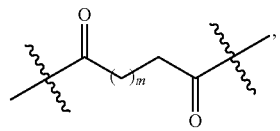

wherein the polymer comprises the structure:

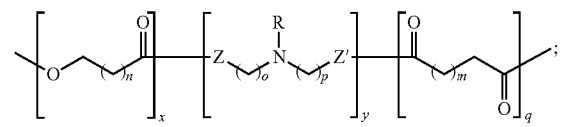

wherein w and f are independently integers from 0-1000;
x, y, and q are independently integers from 1-1000;
wherein h is an integer from 1 to 1000;
wherein n is an integer from 1-30;
wherein m, o, and p are independently an integer from 1-20;
Z and Z' are independently O or NR', wherein R and R' are independently hydrogen, substituted or unsubstituted alkyl, or substituted or unsubstituted aryl; and
wherein the percent composition of the lactone unit is between about 30% and about 100%, calculated as the mole percentage of the total number of moles of the lactone unit divided by the sum of the total number of moles of the lactone unit and either the total number of moles of the diacid or the total number of moles of the diester, or
wherein the molar ratio of the total number of moles of the lactone unit divided by the sum of the total number of moles of the lactone unit and either the total number of moles of the diacid or the total number of moles of the diester is between about 0.3 and about 1.

2. The solid polymeric nanoparticle of claim 1, wherein the number of carbon atoms in the lactone unit of the polymer is between about 10 and about 24.

3. The solid polymeric nanoparticle of claim 1 prepared by double emulsion.

4. The solid polymeric nanoparticle of claim 1, further comprising an active agent encapsulated, entrapped, embedded, or dispersed therein, or complexed thereto.

5. The solid polymeric nanoparticle of claim 4, wherein the active agent is a polynucleotide.

6. The solid polymeric nanoparticle of claim 5, wherein the polynucleotide is composed of DNA, RNA, synthetic nucleotides, or a combination thereof.

7. The solid polymeric nanoparticle of claim 6, wherein the polynucleotide is composed of RNA.

8. The solid polymeric nanoparticle of claim 6, wherein the polynucleotide is an siRNA or an siRNA mimic.

9. A method of delivering an active agent to cells comprising contacting the cells with an effective amount of the solid polymeric nanoparticle of claim 4 and pharmaceutically acceptable carrier.

10. The method of claim 9 wherein the contacting occurs in vitro.

11. The method of claim 9 wherein the contacting occurs in vivo.

12. The method of claim 9, wherein the cells express a target gene, the active agent is an inhibitory nucleic acid that reduces expression of the target gene, or transcript, or protein thereof, and the cells are contacted with an effective amount of a pharmaceutical composition to reduce expression of the target gene, or transcript, or protein thereof in the cells.

13. The method of claim 12, wherein the inhibitory nucleic acid is siRNA.

14. The method of claim 12, wherein the contacting occurs in vivo.

15. The method of claim 12, wherein the solid polymeric nanoparticle is administered to a subject in need thereof in an effective amount for the inhibitory nucleic acid to reduce one or more disease or disorder symptoms in the subject.

16. The method of claim 15, wherein reduced expression of the target gene in the subject is sustained for at least 2 weeks.

* * * * *